United States Patent

Nakajima et al.

[11] Patent Number: 5,808,055
[45] Date of Patent: Sep. 15, 1998

[54] COPPER CATALYZED PROCESS FOR PRODUCING 4-SUBSTITUTED AZETIDINONE DERIVATIVES

[75] Inventors: Masashi Nakajima, deceased, late of Toyama-ken, by Michiko Nakajima, heir; Yasuharu Kimura; Kiyohito Imai, both of Toyama-ken, all of Japan

[73] Assignees: Suntory Limited, Osaka; Nippon Soda Co., Ltd., Tokyo, both of Japan

[21] Appl. No.: 498,499

[22] Filed: Jul. 5, 1995

Related U.S. Application Data

[63] Continuation of Ser. No. 339,221, Nov. 9, 1994, abandoned, which is a continuation of Ser. No. 39,793, Mar. 30, 1993, abandoned.

[30] Foreign Application Priority Data

Mar. 30, 1992 [JP] Japan ............................ 4-073771

[51] Int. Cl.[6] ............................................. C07D 205/09
[52] U.S. Cl. ............................................. 540/357
[58] Field of Search ............................................. 540/357

[56] References Cited

U.S. PATENT DOCUMENTS 5,026,844 6/1991 Ishiguro ............................ 540/357

FOREIGN PATENT DOCUMENTS 0188247 7/1986 European Pat. Off. .

OTHER PUBLICATIONS

Ray, Indian J. Chem 13, 1086, Oct. 1975.

Primary Examiner—Mark L. Berch
Attorney, Agent, or Firm—Cushman, Darby & Cushman, IP Group of Pillsbury, Madison & Sutro

[57] ABSTRACT

A process for producing a 4-substituted azetidinone derivative represented by the following general formula [III]:

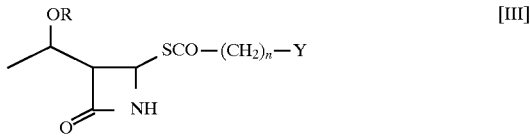

(wherein OR is a protected hydroxy group, Y is an alkyl group, an alkoxy group, a silyloxy group, a carbamoyloxy group, an amino group, a substituted or unsubstituted aromatic group or a substituted or unsubstituted heterocyclic group, and n is an integer of 0 or 1, provided that n does not represent 0 when Y is an alkoxy group, silyloxy group, carbamoyloxy group or amino group), characterized in that a 2-azetidinone derivative represented by the following general formula [I]:

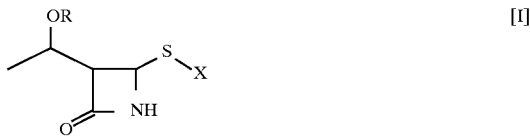

(wherein OR is as defined above, and X is an alkyl group or a substituted or unsubstituted aromatic group) is reacted with thiocarboxylic acid represented by the following general formula [II]:

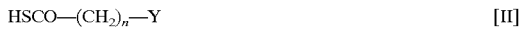

$$\text{HSCO}-(\text{CH}_2)_n-\text{Y} \quad [\text{II}]$$

(wherein Y and n are respectively as defined above) in an organic solvent in the presence of copper compounds.

6 Claims, No Drawings

COPPER CATALYZED PROCESS FOR PRODUCING 4-SUBSTITUTED AZETIDINONE DERIVATIVES

This is a continuation of application Ser. No. 8/339,221, filed on Nov. 9, 1994, which was abandoned upon the filing hereof; which was a continuation of 08/039,793 filed Mar. 30, 1993, now abandoned.

The aforementioned method can shorten the production process compared with the prior method. It is also highly advantageous from an industrial point of view because it does not employ mercury salts.

The present invention relates to a process for producing a 4-substituted azetidinone derivative which is important as an intermediate for preparing penem compounds.

According to the common prior method for producing a 4-substituted azetidinone derivative represented by the following general formula [III]:

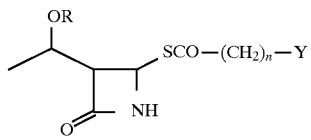

(wherein OR is a protected hydroxyl group and Y is an alkyl group, alkoxy group, silyloxy group, carbamoyloxy group, amino group, a substituted or unsubstituted aromatic group or a substituted or unsubstituted heterocyclic group and n represents an integer of 0 or 1, provided that n does not represent 0 when Y is an alkoxy group, silyloxy group, carbamoyloxy group or amino group), a 2-azetidinone derivative represented by the following general formula [I]:

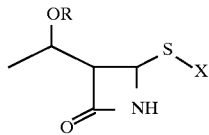

(wherein OR is as defined above, and X is an alkyl group or a substituted or unsubstituted aromatic group) is transformed to a 4-acyloxy compound or 4-arylsulfone, and the transformed compound is further reacted with thiocarboxylic acid represented by the following general formula [II]:

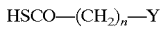

(wherein Y and n are respectively as defined above).

In the above production method, it is preferable to transform 2-azetidinone derivative to a highly reactive acyloxy group, and it is reported in a literature (A. Toshida et al., Chem. Pham. Bull. 29, 2899) that the transformation can be carried out by employing mercury salts.

However, considering the toxicity of mercury salts, such a method is not desirable for industrial production. Furthermore, the use of mercury salts increases the number of required production procedures.

The present inventors have conducted extensive research into industrially producing a 4-substituted azetidinone derivative represented by the general formula [III] without using mercury salts. As a result, they have found that said problems can be solved by carrying out the reaction in the presence of copper compounds.

Thus, the present invention was accomplished on the basis of the finding.

The present invention relates to a process for producing a 4-substituted azetidinone derivative represented by the following general formula [III]:

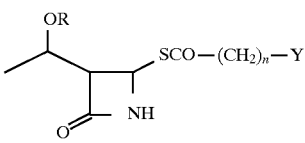

(wherein OR, Y and n are respectively as defined above), characterized in that a 2-azetidinone derivative represented by the following general formula [I]:

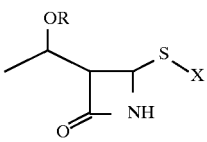

(wherein OR and X are as defined above) is reacted with thiocarboxylic acid represented by the following general formula [II]:

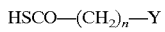

(wherein Y and n are as defined above) in an organic solvent in the presence of copper compounds.

More specifically, a 2-azetidinone derivative represented by the general formula [I] is reacted with thiocarboxylic acid represented by the general formula [II] in toluene, methylene chloride, acetonitrile or a solvent consisting of a combination thereof in the presence of copper compounds such as copper oxides (copper (I) oxide and copper (II) oxide) and copper salts of organic carboxylic acids, for example, copper salts of aliphatic carboxylic acids such as copper (I) acetate, copper (II) acetate, copper propionate, copper butyrate, and the like, and copper salts of aromatic carboxylic acids such as copper benzoate, and the like, preferably copper (I) oxide. The reaction temperature is preferably 0°–70° C., more preferably 10°–30° C. As for the molar ratio of reaction, 1 mol of a 2-azetidinone derivative represented by the formula [I] is reacted with preferably 1–1.5 mol of thiocarboxylic acid represented by the formula [II] and preferably at least 0.5 mol of copper (I) oxide, more preferably 0.6–1.5 mol.

Preferred examples of Y may be an alkyl group such as methyl group and ethyl group, an alkoxy group such as methoxy group and ethoxy group, a silyloxy group such as a tert-butyldiphenylsilyloxy group, a carbamoyloxy group, an amino group, and an aromatic group or a heterocyclic group such as phenyl group, 2-(1-methyl) pyrrolyl group, tetrahydrofuryl group, tetrahydropyranyl group, 1,4-dioxanyl group, 5-oxo-oxolanyl group, 2-oxo-1,3-dioxolanyl group and 1,3-dioxolanyl group, etc.

A protected hydroxyl group represented by OR may be a tert-butyldimethylsilyloxy group, a tert-butyldiphenylsilyloxy group, a dimethylcumylsilyloxy group, a triisopropylsilyloxy group, a dimethylhexylsilyloxy group, a p-nitrobenzyloxycarbonyloxy group, a p-methoxybenzyloxycarbonyloxy group, an allyloxycarbonyloxy group, an acetoxy group, a benzoyloxy group, a tetrahydropyranyloxy group, etc.

Since the alkyl group or substituted or unsubstituted aromatic group represented by X is eliminated together with S adjacent thereto as a result of the reaction of the present invention, X may be any group as long as it does not hinder the reaction. However, a lower alkyl group with 1 to 4 carbon atoms such as methyl, ethyl, propyl or a butyl group, or an aromatic group such as a phenyl group, an alkylphenyl or an alkoxyphenyl group, with an alkyl group having 1 to 4 carbon atoms, or a halophenyl group is preferred from the viewpoint of availability and cost.

When the reaction is complete, precipitated insoluble matter is filtered off. Upon concentration of the filtrate, the filtrate is diluted with an organic solvent such as pentane, hexane, etc. The insoluble matter is filtered off again, and the filtrate is then washed with water and concentrated to obtain crystals containing the intended subject compound represented by the formula [III]. Although the thus obtained products can be used as a raw material for the succeeding process as it is, it may be purified by recrystallization, column chromatography, etc. if necessary.

EXAMPLES

The present invention will be further explained by way of examples.

Example 1
Preparation of (3S,4R)-3-[(R)-1-(tert-butyldimethylsilyloxy) ethyl]-4-[(R)-2-tetrahydrofuranoylthio]-2-azetidinone

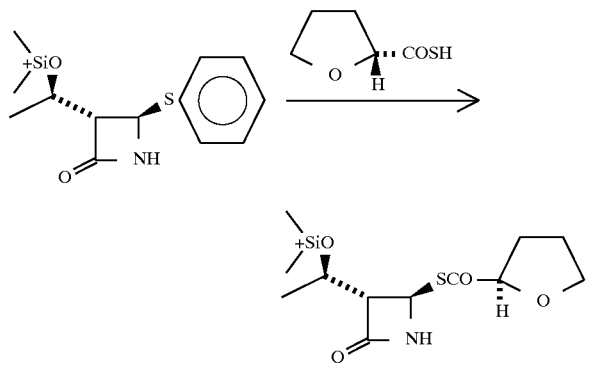

(3S,4R)-3-[(R)-1-(tert-butyldimethylsilyloxy)ethyl]-4-phenylthio-2-azetidinone (10.1 g, 30 mmol) was mixed with acetonitrile (45 ml) and methylene chloride (75 ml), and then, (2R)-tetrahydrofuran-2-thiocarboxylic acid (5.4 g, 41 mmol) was added dropwise into the resulting mixture at 20° C. Copper (I) oxide (3.5 g, 24 mmol) was added by portions over 4.5 hours at 20° C. The resulting mixture was allowed to stand for 2.5 hours.

After the reaction was complete, 1 g of hyflo Super-Cel (manufactured by Jons-Manvill Sales Corp.) was added to the mixture. Insoluble matter was filtered off, and upon concentration of the filtrate, 90 ml of hexane was added to the concentrated filtrate. The insoluble matter was further filtered off, and the filtrate was then washed with water and dried. Upon concentration of the dried matter, 11.1 g of the subject compound [III] in the form of a crystalline substance (purity 92.0%) was obtained.

Yield; 94.7%

Example 2
Preparation of (3S,4R)-3-[(R)-1-(tert-butyldimethylsilyloxy) ethyl]-4-[(R)-2-tetrahydrofuranoylthio]-2-azetidinone 15 ml of acetonitrile, 15 ml of toluene and 0.8 g of copper (I) oxide (5.6 mmol) were added to (3S,4R)-3-[(R)-1-(tert-butyldimethylsilyloxy)ethyl]-4-phenylthio-2-azetidinone (2.7 g, 8.0 mmol), and (2R)-tetrahydrofuran-2-thiocarboxylic acid (1.2 g, 9.1 mmol) was added dropwise into the resulting mixture at 10° C. while being stirred.

The mixture was allowed to stand for 4 hours at 10° C. and another 2 hours at 20°–25° C. After the reaction was complete, insoluble matter was filtered off. Upon concentration of the filtrate, toluene was added to the concentrated filtrate for dilution. The insoluble matter was filtered off again, and the filtrate was washed with water and dried. Upon concentration of the thus obtained matter, 3.0 g of the subject compound [III] was obtained in the form of a crystalline substance (purity 92.3%).

Yield; 96.3%

Example 3
Preparation of (3S,4R)-3-[(R)-1-(tert-butyldimethylsilyloxy) ethyl]-4-[(3-tetrahydrofuranyl) methylcarbonylthio]-2-azetidinone

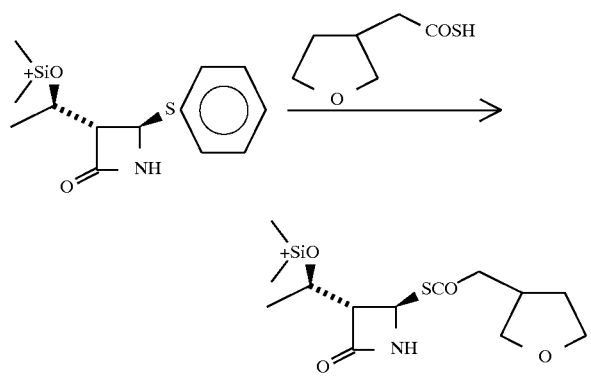

15 ml of acetonitrile, 15 ml of toluene and 0.86 g of copper (I) oxide (6.0 mmol) were added to (3S,4R)-3-[(R)-1-(tert-butyldimethylsilyloxy)ethyl]-4-phenylthio-2-azetidinone (2.7 g, 8.0 mmol). Tetrahydrofuran-3-thio acetic acid (1.3 g, 8.9 mmol) was added dropwise into the mixture at 10° C. while being stirred. The resulting mixture was allowed to stand for 6 hours at 20°–25° C.

After the reaction was complete, insoluble matter was filtered off. Upon concentration of the filtrate, toluene was added to the concentrated filtrate for dilution. The insoluble matter was filtered off again, and the filtrate was washed with water and dried. Upon concentration of the thus obtained matter, 3.1 g of the subject compound [III] was obtained in the form of crystalline substance (purity 90.4%).

Yield; 93.8%

Example 4
Preparation of (3S,4R)-3-[(R)-1-(tert-butyldimethylsilyloxy)ethyl]-4-(acetylthio)-2-azetidinone

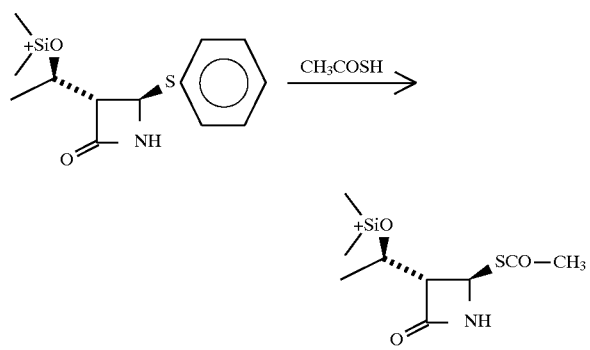

1 ml of acetonitrile, 1 ml of toluene and 107 mg of copper (I) oxide (0.75 mmol) were added to (3S,4R)-3-[(R)-1-(tert-butyldimethylsilyloxy)ethyl]-4-(phenylthio)-2-azetidinone (169 mg, 0.50 mmol). 43 mg of thio acetic acid (0.56 mmol) was further added to the resulting mixture, and the mixture was stirred for 8 hours at room temperature.

After the reaction was complete, insoluble matter was filtered off. The filtrate was purified by silica gel chromatography (eluent; hexane:ethyl acetate =4:1) to obtain 129.4 mg of the subject compound [III] in the form of colorless crystalline substance.

Yield; 85.3%

Example 5
Preparation of (3S,4R)-3-[(R)-1-(tert-butyldimethylsilyloxy) ethyl]-4-[2-(diphenyl-tert-butylsilyloxy)acetylthio]-2-azetidinone

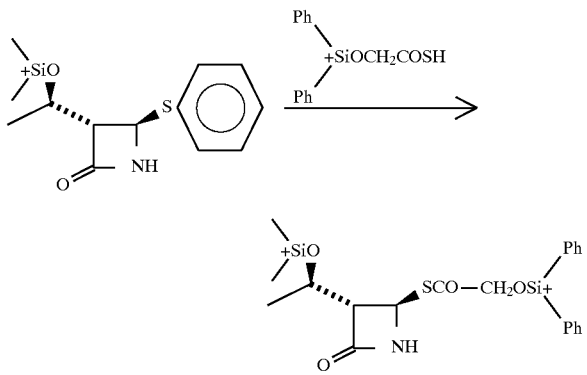

0.9 ml of acetonitrile, 0.9 ml of toluene and 100 mg of copper (I) oxide (0.7 mmol) were added to (3S,4R)-3-[(R)-1-(tert-butyldimethylsilyloxy)ethyl]-4-(phenylthio)-2-azetidinone (155 mg, 0.46 mmol). 200 mg of 2-diphenyl-tert-butylsilyloxythio acetic acid (0.59 mmol) was further added, and the resulting mixture was stirred for 1 hour at room temperature. Upon completion of the reaction, insoluble matter was filtered off. The filtrate was purified by silica gel chromatography (eluent; hexane:ethyl acetate=6:1) to obtain 225 mg of the subject compound [III] in the form of a colorless crystalline substance.

Yield; 85.4%

Example 6
Preparation of (3S,4R)-3-[(R)-1-(tert-butyldimethylsilyloxy)ethyl]-4-(2-methoxyacetylthio)-2-azetidinone

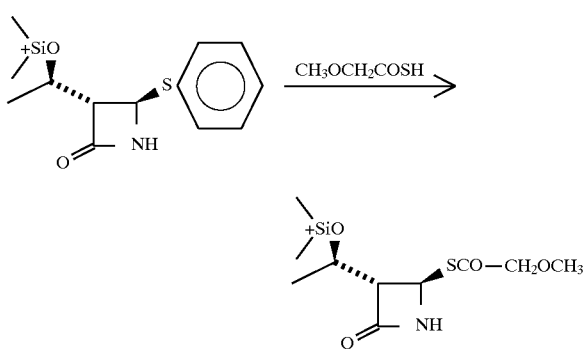

1 ml of acetonitrile, 1 ml of toluene and 72 mg of copper (I) oxide (0.50 mmol) were added to (3S,4R)-3-[(R)-1-(tert-butyldimethylsilyloxy)ethyl]-4-(phenylthio)-2-azetidinone (169 mg, 0.50 mmol), and 80 mg of 2-methoxymethylthio carboxylic acid (0.75 mmol) was further added to the mixture while being stirred. The resulting mixture was stirred for 6 hours at room temperature. Upon completion of the reaction, insoluble matter was filtered off, and the filtrate was purified by silica gel chromatography (eluent; hexane-:ethyl acetate=4:1) to obtain 138 mg of the subject compound [III] in the form of a colorless crystalline substance.

Yield; 76.8%

Example 7
Preparation of (3S,4R)-3-[(R)-1-(tert-butyldimethylsilyloxy)ethyl]-4-(benzoylthio)-2-azetidinone

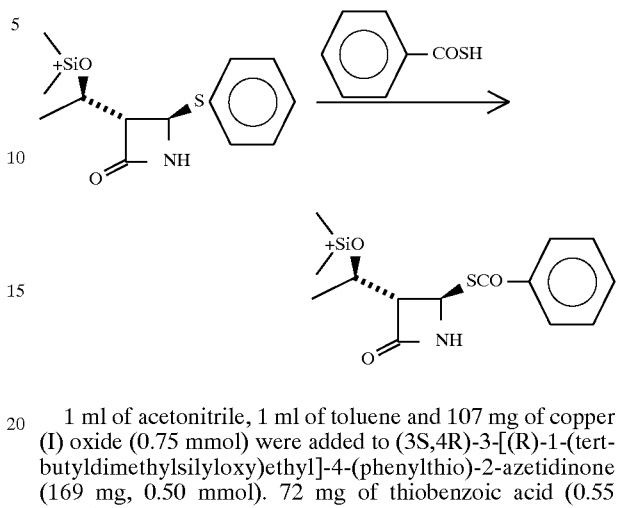

1 ml of acetonitrile, 1 ml of toluene and 107 mg of copper (I) oxide (0.75 mmol) were added to (3S,4R)-3-[(R)-1-(tert-butyldimethylsilyloxy)ethyl]-4-(phenylthio)-2-azetidinone (169 mg, 0.50 mmol). 72 mg of thiobenzoic acid (0.55 mmol) was further added while being stirred, and the mixture was stirred for 6 hours at room temperature. Upon completion of the reaction, insoluble matter was filtered off, and the filtrate was purified by silica gel chromatography (eluent; hexane:ethyl acetate=4:1) to obtain 166.5 mg of the subject compound [III] in the form of a colorless crystalline substance.

Yield; 91.1%

Example 8
Preparation of (3S,4R)-3-[(R)-1-(tert-butyldimethylsilyloxy) ethyl]-4-(1-methyl-2-pyrrolecarbonylthio)-2-azetidinone

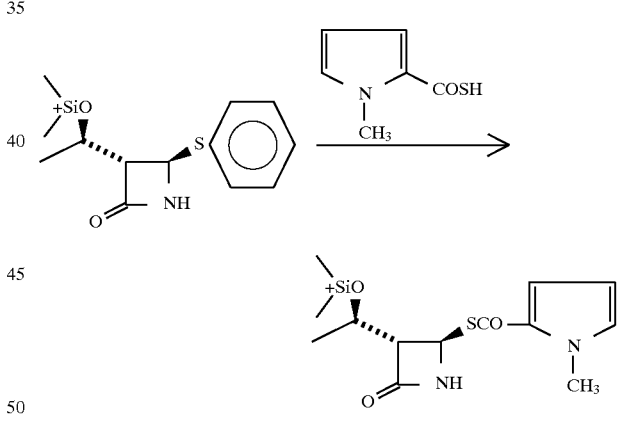

1 ml of acetonitrile, 1 ml of toluene and 107 mg of copper (I) oxide (0.75 mmol) were added to (3S,4R)-3-[(R)-1-(tert-butyldimethylsilyloxy)ethyl]-4-(phenylthio)-2-azetidinone (169 mg, 0.50 mmol). 106 mg of 1-methyl-2-pyrrolethiocarboxylic acid (0.75 mmol) was further added while being stirred, and the resulting mixture was stirred for 24 hours at 70° C. Upon completion of the reaction, insoluble matter was filtered off, the filtrate was purified by silica gel chromatography (eluent; hexane:ethyl acetate=3:1) to obtain 79.3 mg of the subject compound [III] in the form of a colorless crystalline substance (purity: 74%)

Yield; 43.0%

Effects of the Invention

Not only can the method of the present invention shorten the production process compared with the method according to the prior art but it also enables an industrially desirable production of a 4-substituted azetidinone derivative represented by the general formula [III] because copper compounds are employed in place of mercury salts in the present invention.

What is claimed is:

1. A process for producing a 4-substituted azetidinone derivative represented by the formula [III]

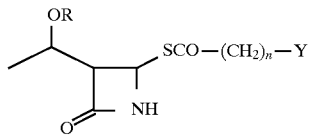

wherein OR is a protected hydroxy group, Y is an alkyl group, an alkoxy group, a silyloxy group, a carbamoyloxy group, an amino group, a phenyl group, 2-(1-methyl) pyrrolyl group, tetrahydrofuryl group, tetrahydropyranyl group, 1,4-dioxanyl group, 5-oxo-oxolanyl group, 2-oxo-1,3-dioxolanyl group or 1,3-dioxolanyl group, and n is an integer of 0 or 1, provided that n does not represent O when Y is an alkoxy group, silyloxy group, carbamoyloxy group or amino group, characterized in that a 2-azetidinone derivative represented by the formula [I]:

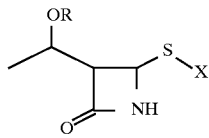

wherein OR is as defined above, and X is an alkyl group, a phenyl group, an alkylphenyl group, an alkoxyphenyl group, or a halophenyl group, is reacted with thiocarboxylic acid represented by the formula [II]:

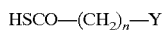 [II]

wherein Y and n are respectively as defined above, in an organic solvent in the presence of copper (I) oxide.

2. A process according to claim 1, wherein the aromatic group or heterocyclic group represented by Y is a phenyl a group, 2-(1-methyl) pyrrolyl group, tetrahydrofuryl group, tetrahydropyranyl group, 1,4-dioxanyl group, 5-oxo-oxolanyl group, 2-oxo-1,3-dioxolanyl group or 1,3-dioxolanyl group.

3. A process according to claim 1, wherein the organic solvent is toluene, methylene chloride, acetonitrile or a solvent consisting of a combination thereof.

4. A process for producing a 4-substituted azetidinone derivative represented by the following formula [III]:

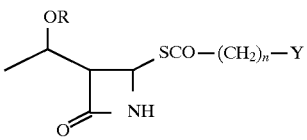

wherein OR is a protected hydroxy group, Y is an alkyl group, an alkoxy group, a silyloxy group, a carbamoyloxy group, an amino group, an alkyl, alkoxy, or halogen substituted or unsubstituted aromatic group, an alkyl substituted or unsubstituted heterocyclic group selected from 2-(1-methyl) pyrrolyl group, tetrahydrofuryl group, tetrahydropyranyl group, 1,4-dioxanyl group, 5-oxo-oxolanyl group, 2-oxo-1,3-dioxolanyl group and 1,3-dioxolanyl group, and n is an integer of 0 or 1, provided that n does not represent O when Y is an alkoxy group, silyloxy group, carbamoyloxy group or amino group, characterized in that a 2-azetidinone derivative represented by the following formula [I]:

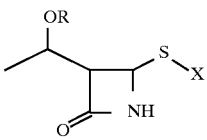

wherein OR is as defined above, and X is an alkyl group, a phenyl group, an alkylphenyl group, an alkoxyphenyl group or a halophenyl group, is reacted at a temperature above 0° C. with thiocarboxylic acid represented by the following formula [II]:

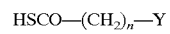

wherein Y and n are respectively as defined above in an organic solvent in the presence of at least 0.5 mol of copper (I) oxide to 1 mol of 2-azetidinone of formula.

5. A process according to claim 4 wherein 1 mol of 2 azetidinone of formula [I] is reacted with 1–1.5 mol of thiocarboxylic acid of formula [II].

6. A process according to claim 4 wherein the reaction is carried out at a temperature of 10°–70° C. and in the presence of 0.6–1.5 mol of copper [I] oxide.

* * * * *